(12) United States Patent
Brennen (10) Patent No.: US 7,159,848 B2
(45) Date of Patent: Jan. 9, 2007

(54) CLAMPING SYSTEMS

(75) Inventor: Reid Alyn Brennen, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 108 days.

(21) Appl. No.: 10/938,485

(22) Filed: Sep. 10, 2004

(65) Prior Publication Data

US 2006/0054849 A1    Mar. 16, 2006

(51) Int. Cl.
*F16K 27/08* (2006.01)

(52) U.S. Cl. .................. 251/367; 251/129.11; 251/304

(58) Field of Classification Search ........... 251/129.11, 251/304, 366, 367; 137/625.11, 625.46
See application file for complete search history.

(56) References Cited

U.S. PATENT DOCUMENTS

| | | | | |
|---|---|---|---|---|
| 3,837,360 A | * | 9/1974 | Bubula | 137/625.46 |
| 5,333,647 A | * | 8/1994 | Fukano et al. | 137/884 |
| 6,497,245 B1 | * | 12/2002 | Torii | 137/315.11 |
| 6,874,756 B1 | * | 4/2005 | Hawkins et al. | 251/291 |

* cited by examiner

*Primary Examiner*—Edward K. Look
*Assistant Examiner*—John K. Fristoe, Jr.

(57) ABSTRACT

Systems having clamping structures are provided.

18 Claims, 7 Drawing Sheets

FIG. 3A
a-a CROSS-SECTION

FIG. 3B
b-b CROSS-SECTION

CLAMPING SYSTEMS

BACKGROUND

Valves traditionally used in high-pressure liquid chromatography (HPLC) systems typically operate under high-pressure (about 1 to 400 bar or higher) and allow switching between inlet and outlet ports or allow a single port to be selectively connected to one or more outlet ports. Due to the high-pressure requirements, large forces need to be applied to the components to maintain a seal between them, which has typically been implemented by using screws to hold the components in place. This method of affixing the components is effective and, depending on the size of the system and the screws, high holding-forces can be generated. In addition, this system works for valve systems that do not need maintenance often or for systems that do not need valve components changed or replaced. There are, however, disadvantages to using screws to provide the high forces necessary to ensure seal formation. First, it is difficult to apply the force directly and evenly between the various components, particularly when tightening and loosening the screws. Because the screws are distributed around the perimeter of a typical interface, it is inherently difficult to tighten the screws such that an even force is applied among the components unless all the screws are tightened simultaneously. Second, if the one or more components need to be removed repeatedly and often, it is time-consuming and possible to damage one or more of the components. Third, once screws are removed from the system, they are loose and subject to misplacement or loss.

Microfluidic devices can be used within HPLC or HPLC-like valves and devices to great effect (U.S. Pat. No. 6,702,256, which is incorporated herein by reference), solving the historically challenging process of connecting traditional fittings and equipment to microscale components. However, using screws to mount these devices is, for the above reasons, undesirable. Thus, for any system that requires frequent and(or easy exchange of parts (e.g., microfluidic devices and HPLC stators) it is preferable to use a method of mounting that does not use screws.

SUMMARY

Briefly described, embodiments of this disclosure include fluidic systems having clamping structure and systems. One exemplary system, among others, includes a valve body, a rotor system located within the valve body, a stator system disposed above the rotor system and on top of the valve body, and a clamping structure. The rotor system and the stator system are adapted to fluidicly communicate. The clamping structure is disposed above the valve body. The clamping structure is moved into a closed position by applying a pressure to the clamping structure. The clamping structure reversibly engages the valve body in the closed position. The clamping structure secures the stator system to the valve body substantially aligned with the rotor system while in the closed position.

Another exemplary system, among others, includes a valve body, a rotor system located within the valve body, a stator system disposed above the rotor system and on top of the valve body, and a clamping structure attached to the valve body via a hinge. The rotor system and the stator system are adapted to fluidicly communicate. The clamping structure is pivoted about the hinge to an open position and a closed position. The clamping structure reversibly engages the valve body in the closed position. The clamping structure secures the stator system to the valve body substantially aligned with the rotor system while in the closed position.

Another exemplary system, among others, includes a valve body having a clamp-latch interface at a first position, a rotor system located within the valve body, a stator system disposed above the rotor system, an alignment structure located between the rotor system and the stator system, and a clamping structure. The rotor system includes a valve rotor. The stator system includes a valve stator. The alignment structure substantially aligns the valve stator and the valve rotor. The clamping structure is attached to the valve body by a pivot structure at a second position. The first position and the second position are at substantially opposite ends of the valve body. The clamping structure is pivoted about the pivot structure to an open position and a closed position. The clamping structure reversibly engages the clamp-latch interface in the closed position. The clamping structure secures the valve stator to the alignment structure and valve body while in the closed position.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

Reference is now made to the following drawings. Note that the components in the drawings are not necessarily to scale.

FIG. 3A is a schematic of the a-a cross-section of a feature of the system illustrated in FIG. 2, while

DETAILED DESCRIPTION

Clamping structures and systems that can be used in microfluidic systems and high-pressure liquid chromatography (HPLC) systems are provided. By way of example, some embodiments provide for a system having a clamping structure attached via a pivot or hinging mechanism (e.g., hinge) to a structure, where the clamping structure can be opened and closed by pivoting about the pivot or hinging mechanism. In addition, the clamping structure can be secured to the structure in the closed position using a securing mechanism (e.g., a latching mechanism or direct force mechanism driven manually, pneumatically, hydraulically, electrically, and/or magnetically). The pivoting and securing mechanisms permit easy and quick securing of the clamping structure to the structure without the need for multiple mounting screws. In particular, multiple mounting screws are cumbersome and slow down the process of changing components of the system. For example, a microfluidic chip that can be incorporated within the microfluidic system to direct fluid flow and/or mix fluid may need to be changed on a regular basis.

As mentioned above, embodiments of the clamping structure incorporate a hinging mechanism (e.g., hinge, fulcrum, and the like) in conjunction with a securing mechanism. In general, the hinging mechanism and the securing mechanism are disposed at substantially opposite ends of the clamping structure, which allows the lever principle to be used to increase the force applied to the components by the securing mechanism. In addition, the clamping structure can be moved to an open or closed position by releasing or securing, respectively, the securing mechanism and moving the clamping structure about the hinging mechanism. The clamping structure is in the open position when the securing mechanism between the clamping structure and the structure is released, while the clamping structure is in the closed position when the securing mechanism between the clamping structure and the structure is secured. When the clamping structure is in the closed position, a substantially sealed fluidic connection is formed in the system among the components therein. Use of the clamping structure overcomes, at least in part, some of the disadvantages associated with using multiple mounting screws because the clamping structure can be moved from the open position to the closed position and vice versa easily and quickly without screwing/unscrewing securing screws.

Figure 1:
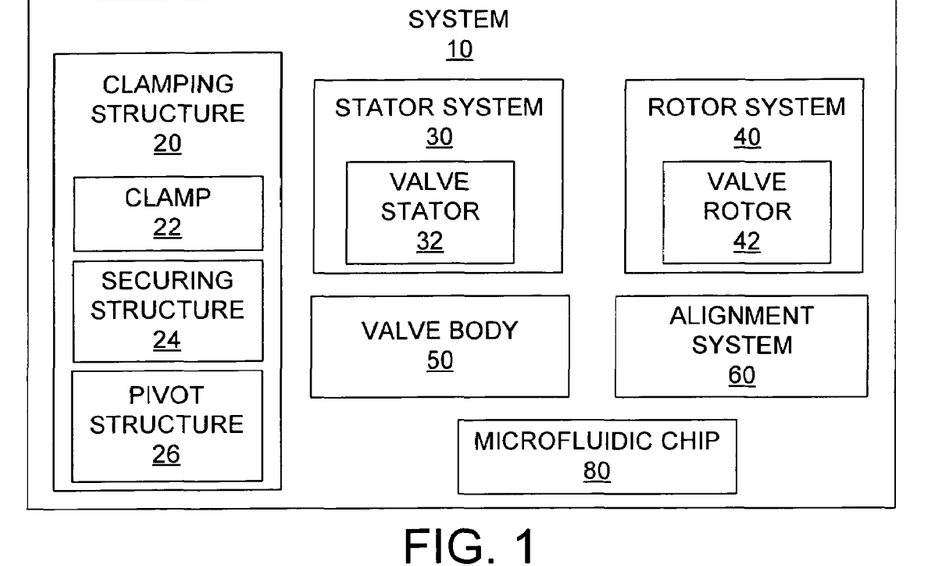
FIG. 1 illustrates a representative embodiment of a system incorporating the clamping structure.

FIG. 1 illustrates a representative embodiment of a system 10 (e.g., a microfluidic system or a HPLC valve system). The system 10 includes, but is not limited to, a clamping structure 20, a stator system 30, a rotor system 40, a valve body 50, and an alignment system 60. The system 10 can be part of, incorporated into, and/or used in conjunction with, systems such as, but not limited to, chromatography systems (e.g., liquid chromatography), chromatography/spectrometry systems, mixing systems, capillary electrophoresis systems, capillary electro-chromatography systems, and combinations thereof.

For example, the system 10 can optionally include a microfluidic chip 80. In this embodiment, the system 10 can be fluidicly connected to a liquid chromatography system via the stator system 30. The fluid from the liquid chromatograph system can flow through the stator system 30 to the microfluidic chip 80 and then to the rotor system 40. The system 10 can be interfaced to a mass spectrometer so that fluid exits the microfluidic chip 80 and flows into the mass spectrometer. In addition, the system may be used in applications such as, but not limited to, sample preparation, chemical reaction, analyte detection, fluid property measurement, sample measurement, and combinations thereof.

In another embodiment, the system 10 includes a microfluidic chip and can be called a "microfluidic system," while in another system the microfluidic chip is not present and the system 10 can be called a "HPLC valve system."

The relationship among the various components is described briefly in relation to FIG. 1, and a more detailed discussion will follow in relation to FIGS. 2 through 7B. In general, the valve body 50 is a housing that contains the rotor system 40, which interfaces with the valve stator system 30 via the alignment system 60. The alignment system 60 is disposed on the top side of the valve body 50 adjacent the rotor system 40. The stator system 30 can be positioned above the rotor system 40. The stator system 30 is substantially aligned with the rotor system 40 by the alignment system 60. The clamping structure 20 is attached to a first pivot point position (e.g., hinge) on the valve body 50. In addition, the clamping structure 20 can also attach to the valve body 50 at substantially the opposite end of the clamping structure 20 using a securing mechanism (e.g., latch mechanism and direct force mechanism), which is described in more detail below.

The clamping structure 20 secures the stator system 30 to the valve body 50 with a substantially fluidic seal between the stator system 30 and the rotor system 40 by reversibly attaching to the valve body using the securing mechanism. When a microfluidic device (e.g., a microfluidic chip) is disposed between the stator system 30 and the rotor system 40, the clamping structure 20 secures the stator system 30 to the valve body 50 and the microfluidic device, as well as secures the microfludic device to the rotor system 40. In each case one or more substantially fluidic seals are formed between the various components. In another embodiment, one or more electrical contacts can be made with the microfluidic device by securing the clamping structure 20 to the valve body 50.

The clamping structure 20 includes, but is not limited to, a clamp 22, a securing structure 24, and a pivot structure 26. The clamping structure 20 can be monolithic or formed of a plurality of components. The pivot structure 26 and the securing structure 24 are disposed at substantially opposite ends of the clamping structure 20. The clamp 22 is between the pivot structure 26 and the securing structure 24. The pivot structure 26 engages the valve body 50 at a first position on the valve body 50 that is on substantially the opposite side of the valve body 50 where the securing structure 24 engages the valve body 50.

Figure 2:
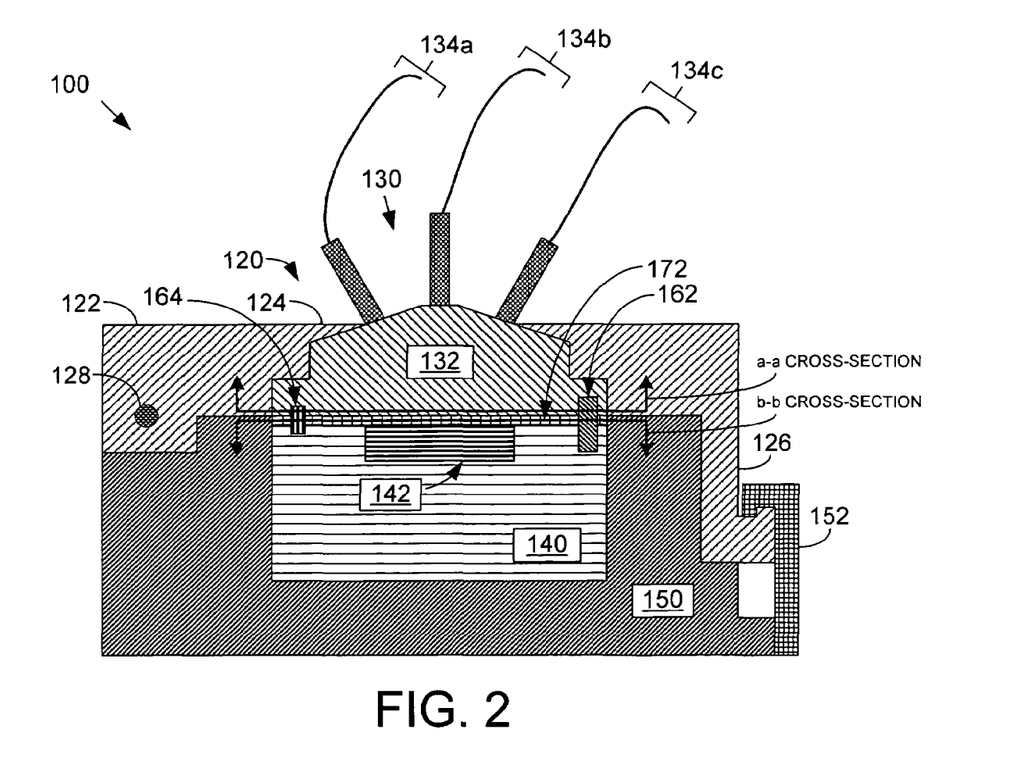
FIG. 2 is a schematic of a representative embodiment of a system.

The stator system 30 includes, but is not limited to, a valve stator 32. The valve stator 32 includes one or more channels that can be used to flow fluid from a fluid source (e.g., liquid chromatograph) to a microfluidic chip disposed within the valve body 50. In particular, the stator system 30 can be in fluidic communication with another device through one or more (three are shown in FIG. 2 as an example) fluid conduits 134a, 134b, and 134c. The clamping structure 20 depresses the valve stator 32 against the valve body 50 and the rotor system 40. As mentioned above, the pressure or force applied by the clamping structure 20 onto the valve stator 32 and the rotor system 40 results in substantially sealed fluidic contacts therein.

The rotor system 40 includes, but is not limited to, a valve rotor 42. The valve rotor 42 is disposed within the valve body 50. The valve stator 32 is disposed above the valve rotor 42 and engages the valve rotor 42 either directly and/or indirectly. In one embodiment, a microfluidic chip 80 is disposed between portions of the valve stator 32 and the valve rotor 42. Subject to proper conditions and orientation, a fluid can flow through the valve stator 32 and through the microfluidic chip 80. The valve rotor 42 can be used to change the orientation and flow of the fluid by rotating such that the features contained therein are disposed differently to the features in the chip.

As mentioned above, the valve body 50 includes, but is not limited to, the body or housing that includes the rotor system 40 and alignment system 60. In addition, the valve body 50 is attached to the clamping structure 20 via a pivot structure 26, such as a hinge. Also the valve body 50 is reversibly attached to the clamping structure 20 at the end opposite the pivot structure 26 using the securing structure 24 of the clamping structure 20 and a clamp-securing interface of the valve body 50.

The alignment system 60 includes, but is not limited to, one or more positioning structures. The positioning structures are adapted to align the valve stator 32 with the valve rotor 42. In addition, the positioning structures are adapted to align a microfluidic chip with the valve rotor 42 and valve stator 32 so that they can fluidicly communicate. In particular, the positioning structure can include one or more alignment structures and one or more pre-alignment structures. The pre-alignment structure aligns the valve stator 32 so that the alignment structure can engage the valve stator 32 and more precisely align the valve stator 32 with the valve rotor 42. In other words, the pre-alignment structure "roughly" aligns the valve stator 32 and the valve rotor 42, while the alignment structure provides a "finer" alignment mechanism of the valve stator 32 and the valve rotor 42.

The valve stator 42 includes one or more alignment orifices that correspond to the positioning structures, and more particularly, the pre-alignment and alignment structures. The alignment orifice receives the positioning structures and therefore guides the valve stator 42 into proper alignment. The alignment orifice and the positioning structures can be designed to ensure proper positioning of the valve stator 32 with the valve rotor 42 upon closing of the clamping structure 20. It should be noted that the positioning structures could be part of the valve stator 42 or the rotor system 40, while the other component has orifices.

Figure 3A:
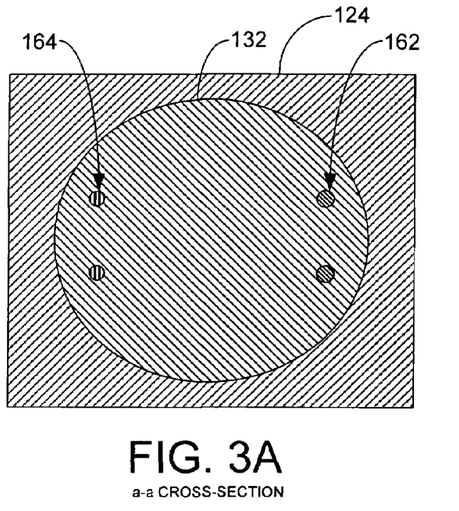
Figure 3B:
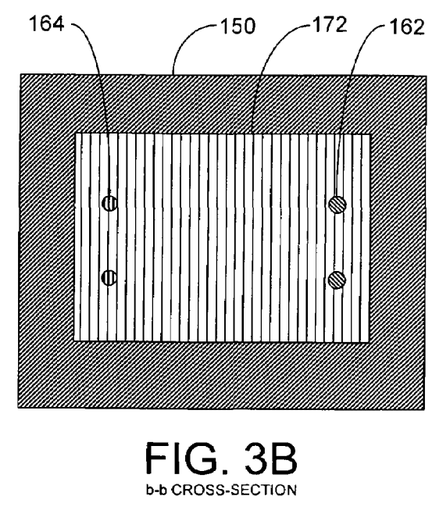
FIG. 3B is a schematic of the b—b cross-section of another feature of the system illustrated in FIG. 2.

FIG. 2 is a schematic of a representative embodiment of a microfluidic system 100. The microfluidic system 100 includes, but is not limited to, a clamping structure 120, a stator system 130, a rotor system 140, a valve body 150, and an alignment system that includes a pair of pre-alignment structures 162 and a pair of alignment structures 164. FIG. 3A is a schematic of the a—a cross-section of FIG. 2 illustrating the valve stator 132, while FIG. 3B is a schematic of the b—b cross-section illustrating the microfluidic chip 172.

A fluid can be flowed into and out of the fluid conduits 134a, 134b, and 134c engaging the stator system 130. In one embodiment, the fluid conduits 134a, 134b, and 134c are part of the stator system 130 and in another embodiment the fluid conduits 134a, 134b, and 134c are separate from the stator system 130.

The clamping structure 120 includes, but is not limited to, a pivot structure 122, a clamp 124, and a latch structure 126. The pivot structure 122 includes a hinge 128 about which the clamping structure 120 pivots. In this embodiment, the clamping structure is monolithic and the pivot structure 122, the clamp 124, and the latch structure 126 represent various portions of the clamping structure 120. The clamp 124 engages the stator system 130, in particular the valve stator 132. As mentioned above, the clamp 124 contacts the valve stator 132 at one or more points and applies pressure thereon to form a substantially fluid-tight seal among the various components while in the closed position.

In addition, the clamping structure 120 engages the valve body 150 via a latch structure 126. The latch structure 126 is engaged by a clamp latch interface 152 which applies the necessary closing force to the clamping structure 120 and secures the clamping structure 120 in place. The latch structure 126 and the clamp latch interface 152 can be easily engaged and released in contrast to screw based attachment systems.

The latching system includes the latch structure 126 and the clamp latch interface 152. The latching system can be, but is not limited to, a mechanical latch, magnetic latch, pneumatically-actuated latch, hydraulically-actuated latch, solenoid-actuated latch, and combinations thereof. The latching system can operate in various mechanisms such as, but not limited to, mechanical mechanisms (e.g., physical engagement of the latch structure 126 and the clamp latch interface 152), magnetic or electrical mechanisms, pneumatic or hydraulic mechanisms, and combinations thereof.

In another embodiment, the clamping structure described above could be replaced by a direct application of force pushing or pulling the stator against the rotor. For example, a direct force can be applied to the stator system 130 such that the force is applied continuously. In another embodiment, the force can be applied continuously by passive means (e.g., springs) and an active force applied only to open the system 40 for exchange of parts, chips, and the like.

The pre-alignment structures 162 and the alignment structures 164 include, but are not limited to, rods, projections, non-threaded structures, and the like, that extend above the valve body 150. The pre-alignment structures 162 and the alignment structures 164 can be of various shapes and sizes to ensure substantial alignment-of the various components. The pre-alignment structures 162 and the alignment structures 164 engage the various components through one or more receiving orifices. In particular, the pre-alignment structures 162 and the alignment structures 164 substantially align the valve stator 132, the microfluidic chip 172, and the valve rotor 142.

Figure 4:
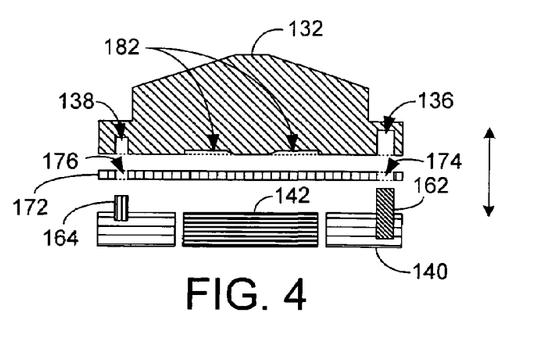
FIG. 4 is a schematic illustrating positional relationships between the various components in the system.

FIG. 4 is a schematic illustrating the positional relationship between the valve stator 132, the microfluidic chip 172, the valve rotor 142, the rotor system 140, and the pre-alignment structure 162 and the alignment structure 164. The microfluidic chip 172 includes one or more pre-alignment orifices 174 and one or more alignment orifices 176 that the pre-alignment structure 162 and the alignment structure 164 pass through during alignment, respectively. The valve stator 132 includes one or more pre-alignment orifices 136 and one or more alignment orifices 138 that the pre-alignment structure 162 and the alignment structure 164 pass through during alignment, respectively.

The clamping structure (not shown) presses the valve stator 132 onto the microfluidic chip 172 and the valve rotor 142. It should be noted that the valve stator includes an indentation 182 that defines a central contact area over which force is applied to/through the microfluidic chip 172 to the valve rotor 142. Given a specific force (upwards in FIG. 4) on the valve rotor 142, the size of the contact area controls the contact pressure between the valve stator 132, the microfluidic chip 172, and the valve rotor 142.

Figure 5:
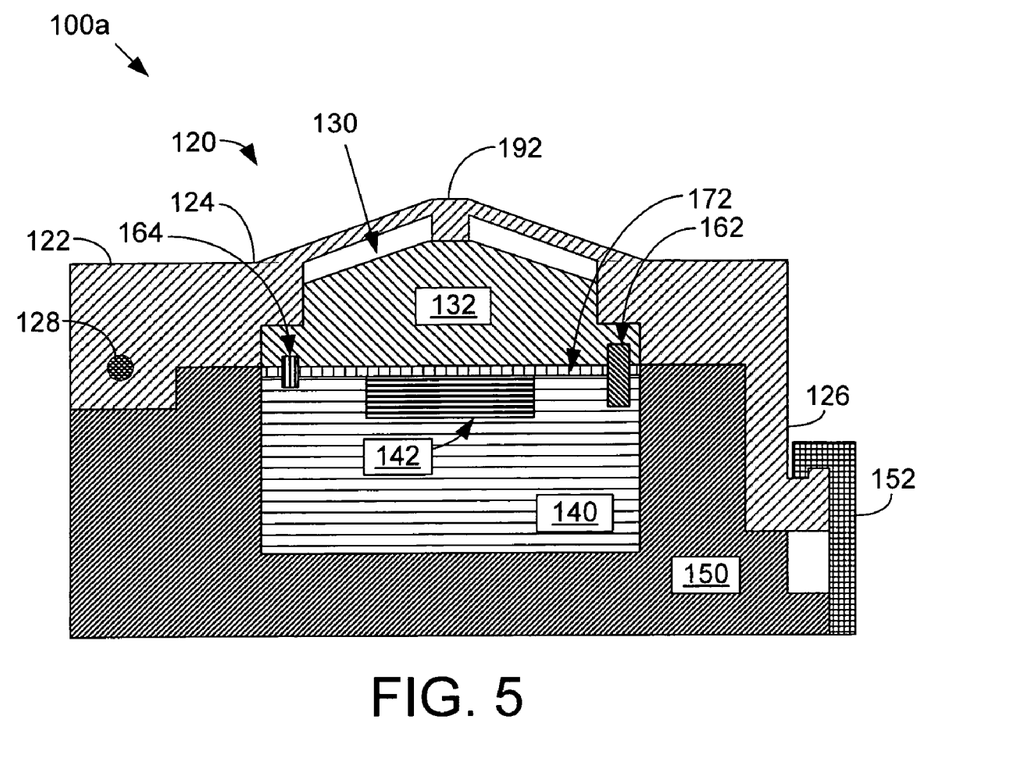
FIG. 5 is a schematic of another embodiment of the system that includes a "spider" clamp.

FIG. 5 is a schematic of another embodiment of the microfluidic system 100a that includes a "spider" clamp 192. In this embodiment, the clamp 124 includes an extension, the spider clamp 192, that contacts the valve stator 132 on the top portion of the valve stator 132. Upon moving the clamping structure 120 into the closed position and engaging the latch structure 126 with the clamp-latch interface 152, the spider clamp 192 depresses the valve stator 132 onto the microfluidic chip 172 and the rotor system 140 forming substantially sealed fluidic connections. The inherent advantage of this method is that the clamp 124 applies the force to the valve stator 132 directly and centrally such that the contact pressure between the valve stator 132, the microfluidic chip 172, and the valve rotor 142 is the same over the whole contact area during the closing and opening of the clamp.

Figure 6A:
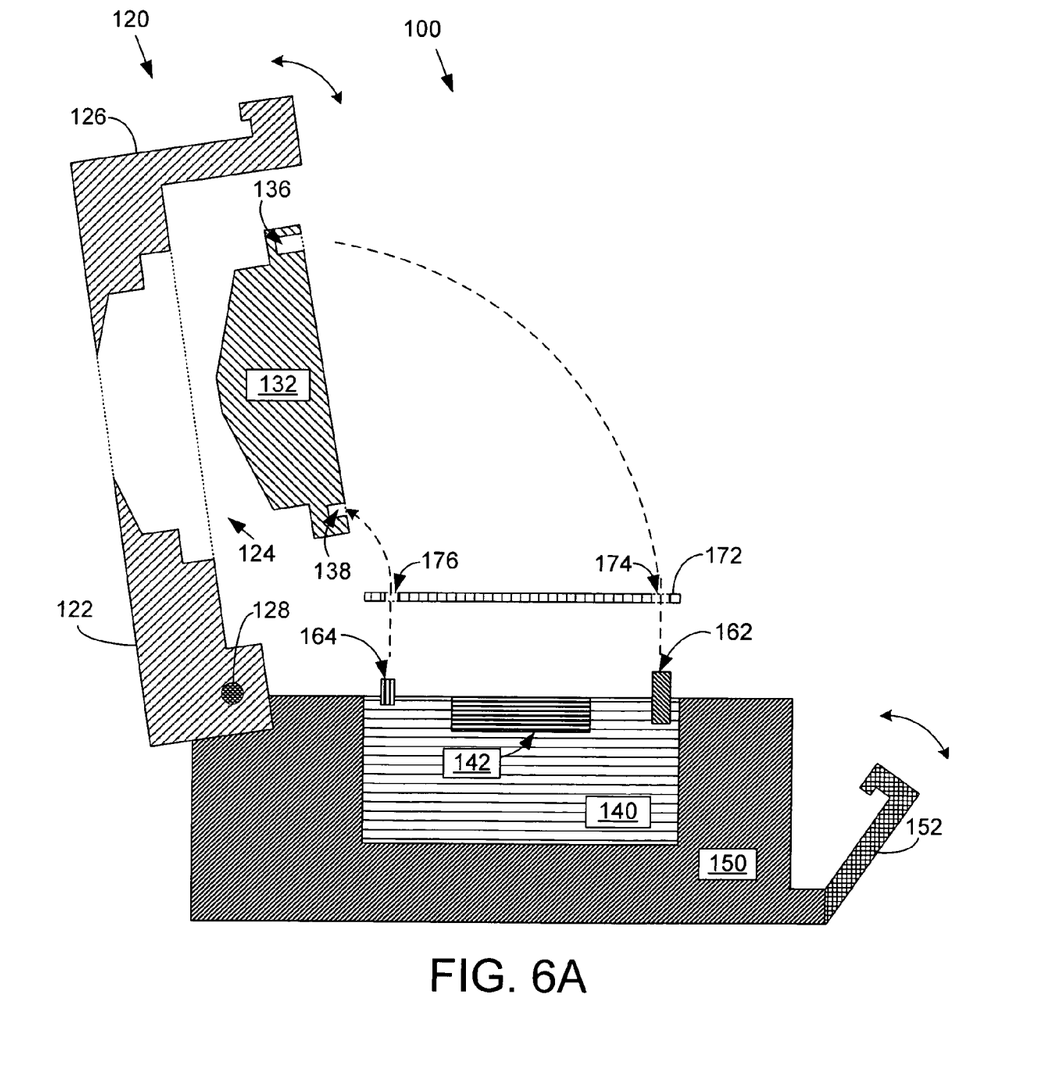
FIGS. 6A through 6C illustrate schematics of the system moving from the open position to the closed position.
Figure 6B:
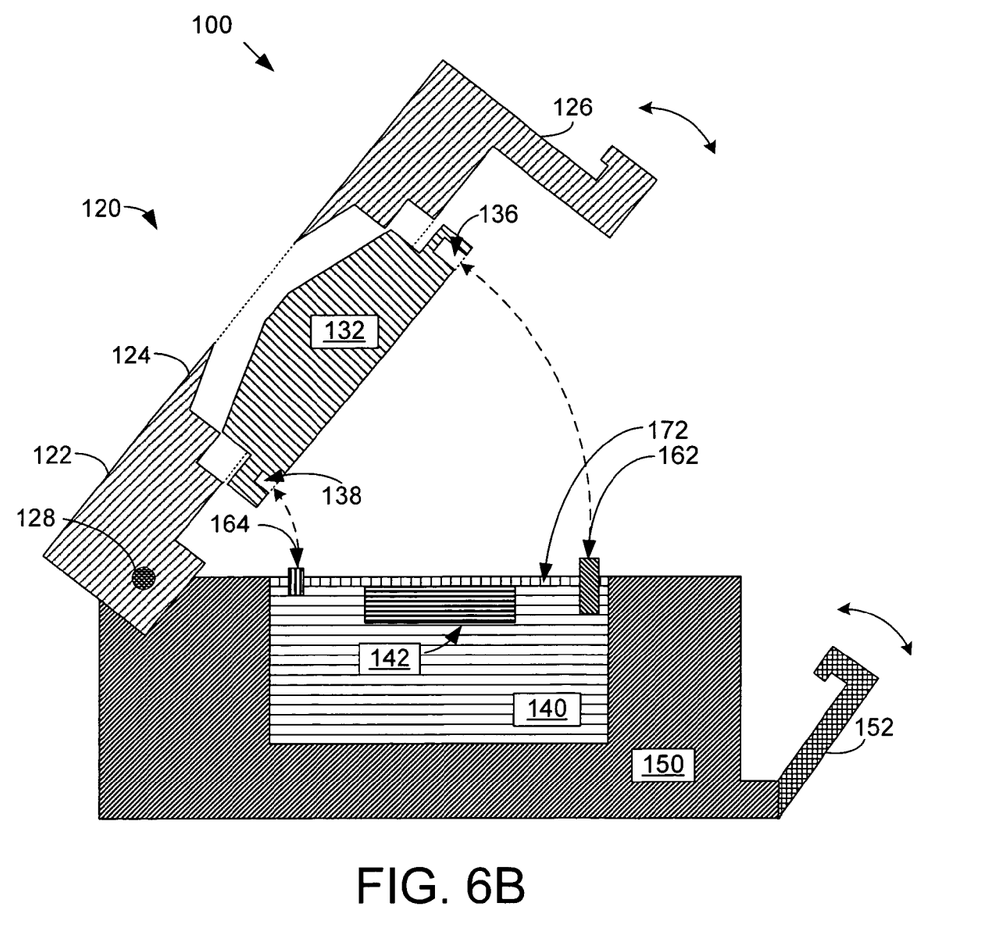
Figure 6C:
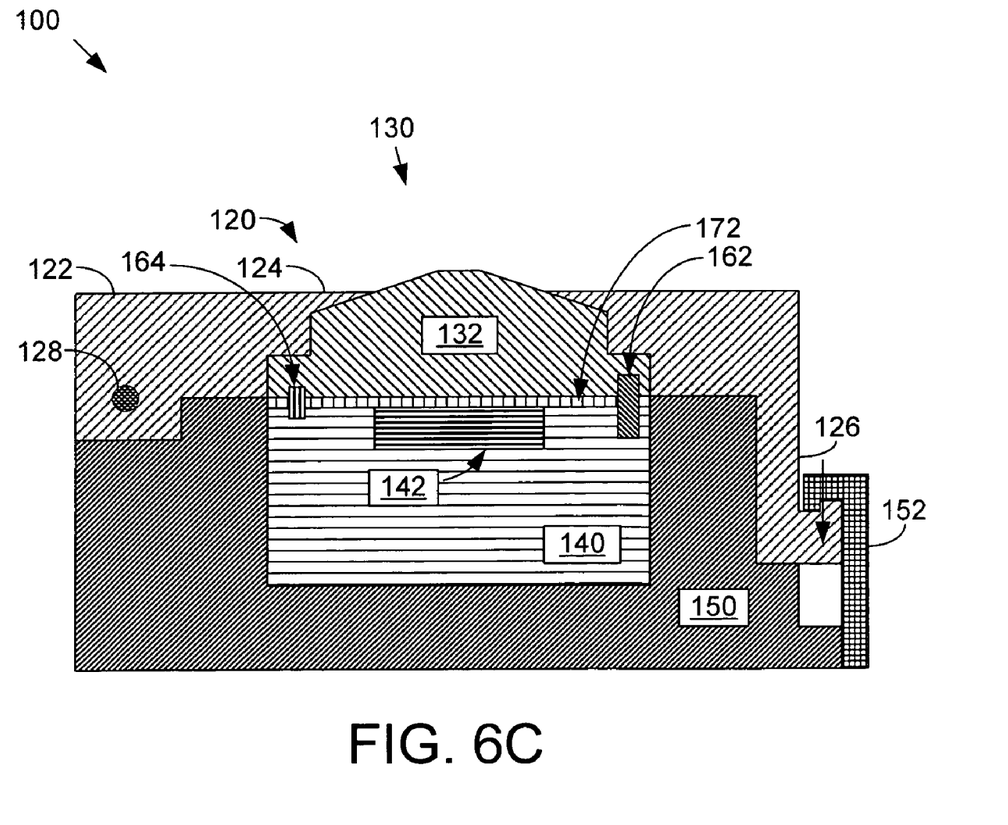

FIGS. 6A through 6C illustrate schematics of the microfluidic system 100 being closed. FIG. 6A is a schematic illustrating the components prior to being closed. FIG. 6B is a schematic illustrating the microfluidic chip 172 disposed on the valve rotor 142 and positioned with the pre-alignment structure 162 and the alignment structure 164. FIG. 6C is a schematic illustrating the microfluidic system 100 in the closed position. In particular, the latch structure 126 engages the clamp-latch interface 152 to secure the valve stator 132 to the valve body 150 and microfluidic chip 172. The clamp-latch interface 152 pivots and also pulls down on the latch structure 126 to strongly force the valve stator 132 against the valve rotor 142. In one embodiment, the valve stator 132 is loosely attached (FIGS. 7A and 7B) to the clamp 124.

Figure 7A:
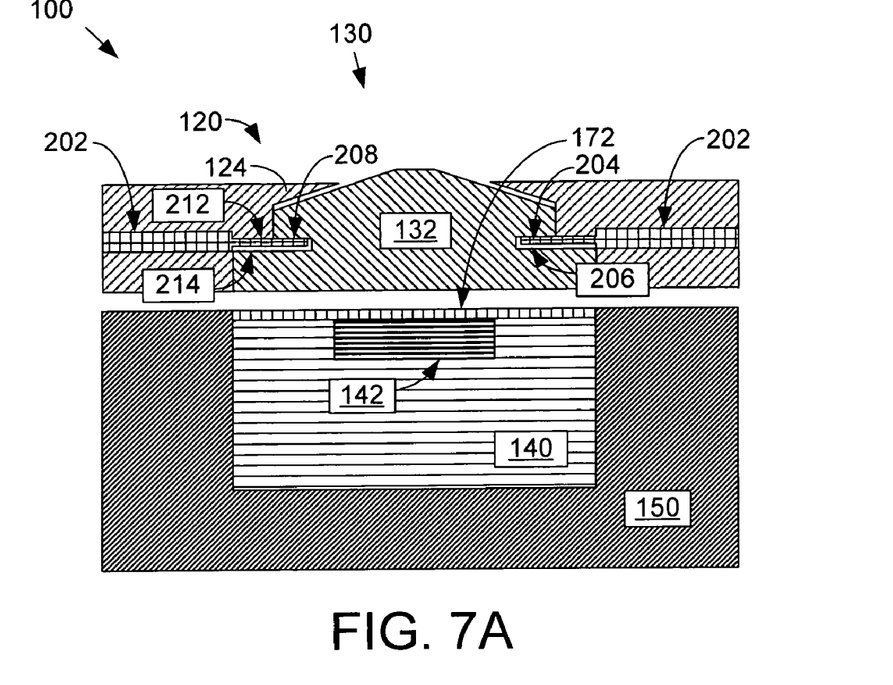
FIGS. 7A and 7B illustrate the use of a limited pivoting attachment method between the valve stator and the clamp.
Figure 7B:
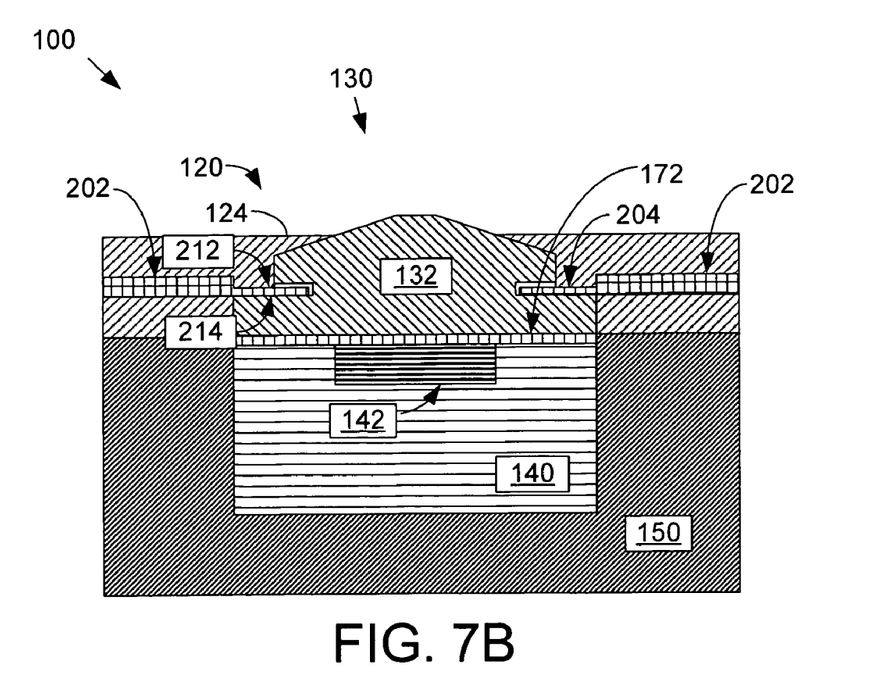

FIG. 7A illustrates the valve stator 132 loosely attached to the clamp 124. Two pins 202 are mounted in the clamp 124 such that each pin end 204 protrudes into a corresponding hole 206 in the valve stator 132. When the clamp 124 is in any open position, the valve stator 132 hangs loosely on the two pins 202, retained by the pin ends 204 contacting the top of the holes 208. During the process of closing the clamp 124, the valve stator 132 contacts the valve body 150 and the valve rotor 142 and/or the microfluidic chip 172. The valve stator 132 stops travelling while the clamp 124 continues closing such that the pin ends 204 contact the stator force surface 214 as shown in FIG. 7B. The force of the clamp 124 is then transmitted through the clamp structure force surface 212 to the pin end 204 and through to the stator force surface 214. One advantage of this embodiment force transmittal lies in the two-point contact between the clamp 124 and the valve stator 132. The axis of rotation of the valve stator 132 as it is mounted in the clamp 124 is parallel to that of the axis of rotation of the clamp 124. This allows the valve stator 132 some limited rotation during the closing rotation of the clamp 124. The limited valve stator 132 rotation allows the bottom face of the valve stator 132 to come to parallel alignment with the top surface of the valve body 150 and the valve rotor 142. Since the valve stator 132 can be parallel to the valve rotor 142, the pressure applied between the valve stator 132 and the valve rotor 142 is substantially even at all times during the closing of the clamp 124.

It should be emphasized that many variations and modifications may be made to the above-described embodiments, including variations is alignment, orientation, and surface contacts. It should be noted that relative positions (e.g., disposed above, on top of, and the like) represent exemplary embodiments, and additional relative positions are covered in other embodiments although not specifically described herein. All such modifications and variations are intended to be included herein within the scope of this disclosure and protected by the following claims.

I claim:

1. A system, comprising:
   a valve body;
   a rotor system located within the valve body;
   a stator system disposed above the rotor system and on top of the valve body, wherein the rotor system and the stator system are adapted to fluidicly communicate;
   a clamping structure disposed above the valve body and attached to said valve body by a pivot structure, wherein the clamping structure is moved into a closed position by applying a pressure to the clamping structure, wherein the clamping structure reversibly engages the valve body in the closed position, and wherein the clamping structure secures the stator system to the valve body substantially aligned with the rotor system while in the closed position.

2. The system of claim 1, further comprising an alignment structure located between the rotor system and the stator system, wherein the alignment structure substantially aligns the stator system and the rotor system while the clamping structure is positioned in the closed position.

3. The system of claim 1, wherein the rotor system includes a valve rotor, wherein the stator system includes a valve stator, and wherein the alignment structure substantially aligns the valve stator and the valve rotor.

4. The system of claim 3, further comprising a microfluidic chip disposed between the valve stator and the valve rotor and in fluidic communication with the valve stator and the valve rotor.

5. The system of claim 3, wherein the valve stator includes at least one positioning orifice and the alignment structure includes at least one positioning structure, and wherein the positioning orifice is adapted to receive the positioning structure.

6. The system of claim 5, wherein the positioning structure includes at least one pre-alignment structure and at least one alignment structure, wherein the valve stator includes at least one pre-alignment positioning orifice and at least one alignment positioning orifice, wherein the pre-alignment positioning orifice is adapted to receive the pre-alignment structure, and wherein the alignment positioning orifice is adapted to receive the alignment structure.

7. The system of claim 5, wherein the valve stator and the valve rotor are substantially aligned by the pre-alignment structure and the alignment structure.

8. A system, comprising:
   a valve body;
   a rotor system located within the valve body;
   a stator system disposed above the rotor system and on top of the valve body, wherein the rotor system and the stator system are adapted to fluidicly communicate;
   a clamping structure attached to the valve body via a hinge, wherein the clamping structure is pivoted about the hinge to an open position and a closed position, wherein the clamping structure reversibly engages the valve body in the closed position, and wherein the clamping structure secures the stator system to the valve body substantially aligned with the rotor system while in the closed position.

9. The system of claim 8, further comprising an alignment structure located between the rotor system and the stator system, wherein the alignment structure substantially aligns the stator system and the rotor system while the clamping structure is positioned in the closed position.

10. The system of claim 9, wherein the rotor system includes a valve rotor, wherein the stator system includes a valve stator, and wherein the alignment structure substantially aligns the valve stator and the valve rotor.

11. The system of claim 10, further comprising a microfluidic chip disposed between the valve stator and the valve rotor and in fluidic communication with the valve stator and the valve rotor.

12. The system of claim 10, wherein the valve stator includes at least one positioning orifice and the alignment structure includes at least one positioning structure, and wherein the positioning orifice is adapted to receive the positioning structure.

13. The system of claim 12, wherein the positioning structure includes at least one pre-alignment structure and at least one alignment structure, wherein the valve stator includes at least one pre-alignment positioning orifice and at least one alignment positioning orifice, wherein the pre-alignment positioning orifice is adapted to receive the pre-alignment structure, and wherein the alignment positioning orifice is adapted to receive the alignment structure.

14. The system of claim 12, wherein the valve stator and the valve rotor are substantially aligned by the pre-alignment structure and the alignment structure.

15. The system of claim 8, wherein the clamping structure includes the hinge, a clamp structure, and a latch structure, wherein the hinge and the latch structure are disposed at substantially opposite ends of the clamping structure, wherein the clamp structure is between the hinge and the latch structure, and wherein the latch structure reversibly engages the valve body in the closed position.

16. A system, comprising:
a valve body having a clamp-latch interface at a first position;
a rotor system located within the valve body, wherein the rotor system includes a valve rotor;
a stator system disposed above the rotor system, wherein the stator system includes a valve stator;
an alignment structure located between the rotor system and the stator system, wherein the alignment structure substantially aligns the valve stator and the valve rotor; and
a clamping structure, wherein the clamping structure is attached to the valve body by a pivot structure at a second position, wherein the first position and the second position are at substantially opposite ends of the valve body, wherein the clamping structure is pivoted about the pivot structure to an open position and a closed position, wherein the clamping structure reversibly engages the clamp-latch interface in the closed position, and wherein the clamping structure secures the valve stator to the alignment structure and valve body while in the closed position.

17. The system of claim 16, wherein the clamping structure includes the pivot structure, a clamp structure, and a latch structure, wherein the pivot structure and the latch structure are disposed at substantially opposite ends of the clamping structure, wherein the clamp structure is between the pivot structure and the latch structure, wherein the pivot structure engages the valve body at a first position on the valve body that is on substantially the opposite side of the valve body as the clamp latch interface, and wherein the latch structure reversibly engages the clamp latch interface in the closed position.

18. The system of claim 16, further comprising a microfluidic chip disposed between the valve stator and the valve rotor and in fluidic communication with the valve stator and the valve rotor.

* * * * *